US00PP35051P2

(12) United States Plant Patent
Valin

(10) Patent No.: US PP35,051 P2
(45) Date of Patent: Mar. 21, 2023

(54) ***BUDDLEIA* PLANT 'TMBU08-3'**

(50) Latin Name: *Buddleia davidii*
Varietal Denomination: TMBU08-3

(71) Applicant: Thopson and Morgan, Ipswich (GB)

(72) Inventor: Charles Valin, Ipswich (GB)

(73) Assignee: Thompson and Morgan

( * ) Notice: Subject to any disclaimer, the term of this patent is extended or adjusted under 35 U.S.C. 154(b) by 31 days.

(21) Appl. No.: 17/849,791

(22) Filed: Jun. 27, 2022

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
See application file for complete search history.

*Primary Examiner* — Annette H Para
(74) *Attorney, Agent, or Firm* — Cassandra Bright

(57) ABSTRACT

A *Buddleia* plant named 'TMBU08-3' is disclosed, characterized by an upright plant habit on plant reaching a medium height for the species. Plants are slow growing, produce light greyed-green foliage and white flowers. Plants are useful for outdoor ornamental purposes, normally produced as an outdoor garden or container plant.

2 Drawing Sheets

Genus and species: *Buddleia davidii.*
Variety denomination: 'TMBU08-3'.

BACKGROUND OF THE INVENTION

'TMBU08-3' is a product of a breeding and selection program for ornamental *Buddleia* varieties to be vegetatively propagated. The new plant of the present invention comprises a new and distinct cultivar of *Buddleia* plant.

'TMBU08-3' is a seedling resulting from the open-pollination of several varieties of *Buddleia davidii*. Seed was bulk collected, without identification of the exact parents. The open-pollination resulting in this new variety was conducted in August of 2014 in Suffolk, UK. The selection of the new variety was made in August of 2015, by the inventor at a research greenhouse located in Suffolk, UK.

'TMBU08-3' was first asexually reproduced by terminal vegetative cuttings at a greenhouse in Suffolk UK, August 2015 and has been asexually reproduced over an approximately three-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices:

1. Upright plant habit.
2. White flowers.
3. Light Greyed-green foliage.
4. Medium mature height.
5. Slow growing.

COMPARISON WITH PARENT VARIETIES

The parent varieties are unidentified.

COMPARISON WITH COMMERCIAL CULTIVARS

'TMBU08-3' can be compared to the commercial variety 'Tobudivory', unpatented. Plants of the two varieties are similar in most horticultural characteristics, however, 'TMBU08-3' differs in the following:

1. Plant form of the new variety is more upright and less spreading than that of 'Tobudivory'.
2. Foliage of the new variety is lighter greyed-green than foliage of this comparator.

'TMBU08-3' can be compared to the commercial variety 'White Ball', unpatented. Plants of the two varieties are similar in most horticultural characteristics, however, 'TMBU08-3' differs in the following:

1. Plant form of the new variety is more upright and less spreading than that of 'White Ball'.
2. Plant height of the new variety is taller than plant height of 'White Ball'.

DESCRIPTION OF THE PHOTOGRAPHS

The present invention of a new and distinct variety of *Buddleia* is shown in the accompanying photographs, the colors being as nearly true as possible with color photographs of this type.

DESCRIPTION OF THE INVENTION

Figure 1:
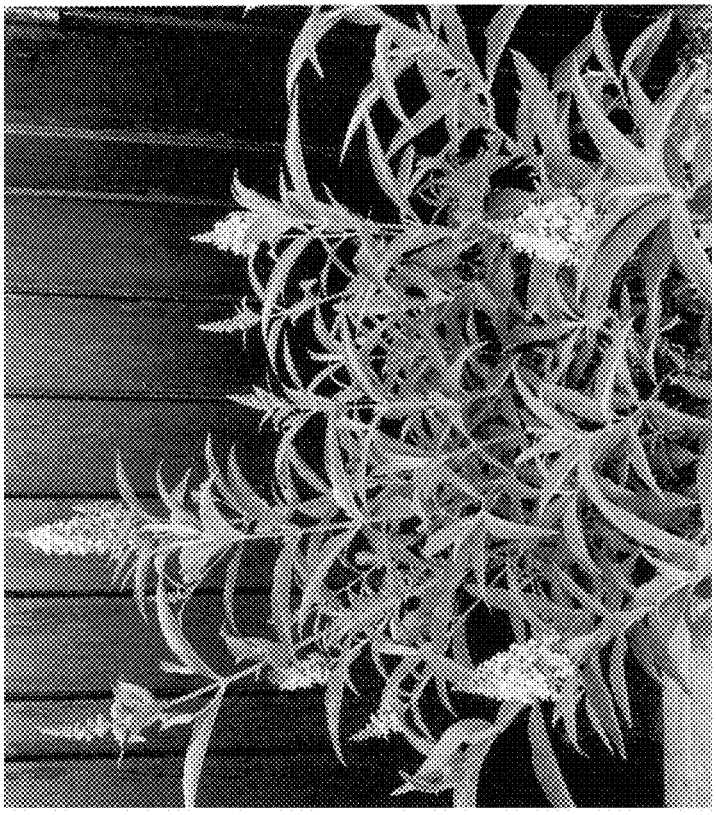
FIG. 1 illustrates a plant of approximately 18 months in a 3 gallon pot
Figure 2:
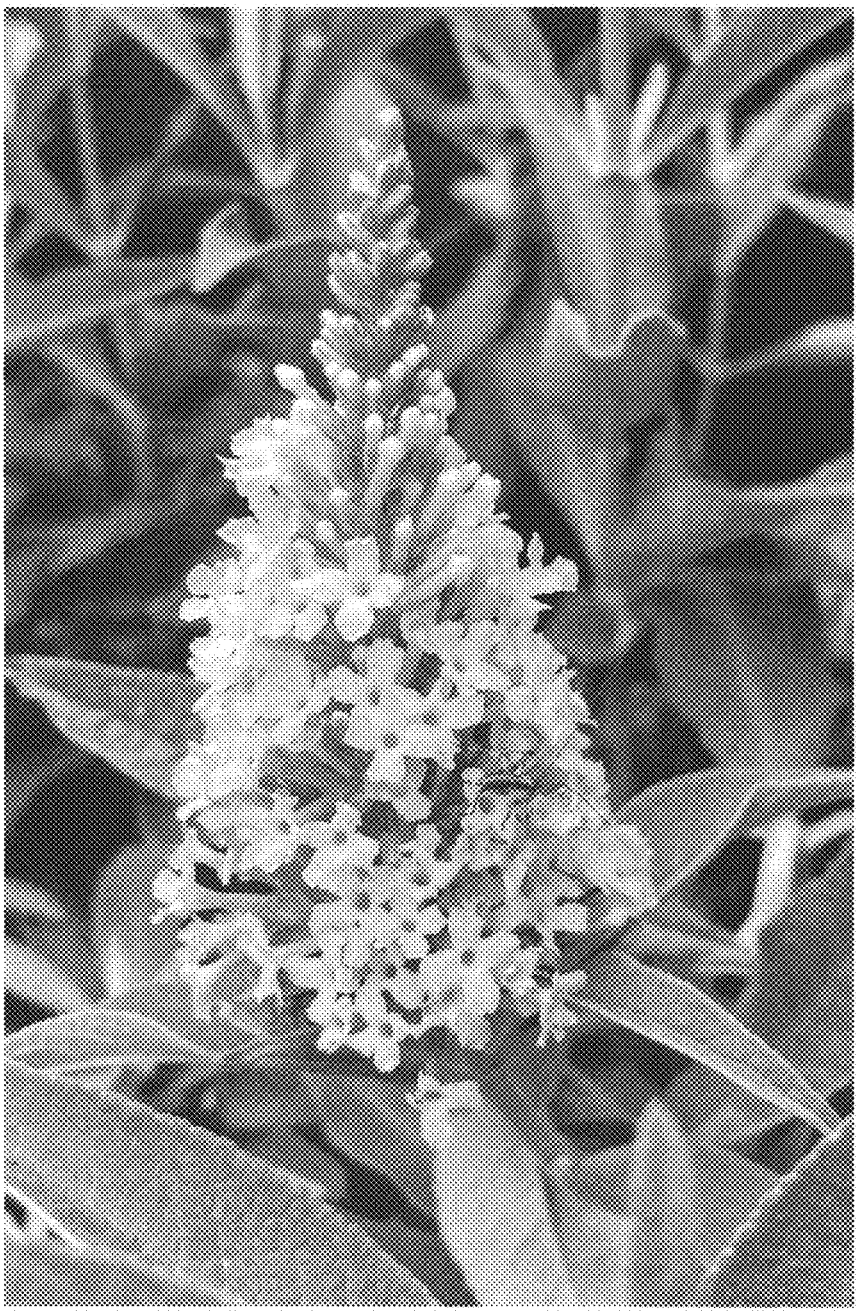
FIG. 2 illustrates a close up of the inflorescence.

This new variety of *Buddleia* is of the botanical classification *Buddleia davidii*. The observations and measurements were gathered from plants grown outdoors in Camarillo, Calif. under natural light, natural day length and temperatures. Measurements were taken during April.

The following is a description of the plant and characteristics that distinguish 'TMBU08-3' as a new and distinct variety. The color designations are taken from the plant itself. Accordingly, any discrepancies between the color designations and the colors depicted in the photographs are due to photographic tolerances. The color chart used in this description is The Royal Horticultural Society color chart, edition 2007.

DETAILED BOTANICAL DESCRIPTION

Classification:
*Botanical.*—*Buddleia davidii.*
*Denomination.*—'TMBU08-3'.

PROPAGATION

Type of propagation typically used: Softwood cutting.
Time to initiate roots: 14-21 days at 21-29° C. average temperature. Time to produce a rooted young plant: 30 days at 21-29° C. average temperature.
Root description: Dense, free-branching, medium thickness, fibrous. Color is white, not accurately described with R.H.S. chart.

PLANT

Age of plant described: 2-3 years from rooted cutting.
Plant type: Flowering perennial shrub.
Container size of the plant described: 3 gallon.
Appropriate containers: 1, 2, 3 gallon commercial pots.
Growth habit: Upright and rounded.
Height: 55 cm.
Plant spread: 55 cm.
Growth rate: Slow.
Plant vigor: Strong.
Characteristics of primary lateral branches:
*Quantity.*—Approximately 12 to 15.
*Branching habit.*—Upright and very slightly outward.
*Branch texture.*—Woody, with pubescence on newer growth. Rounded.
*Length.*—25 to 35 cm.
*Diameter.*—5 mm.
*Color.*—Near RHS Grey-Brown 199C, with pubescence rubbed off, near Greyed-Green 199A with pubescence. Bark near Brown 200C heavily striated near Grey 200C.
*Stem aspect/angle.*—Approximately 0 to 15°.
*Strength.*—Good.
Internode length: 1.0 to 1.8 cm.

FOLIAGE

Leaf:
*Arrangement.*—Opposite, single
*Average length.*—6.1 to 8.9 cm.
*Average width.*—1.8 to 2.5 cm.
*Shape.*—Lanceolate.
*Apex.*—Acute to acuminate.
*Base.*—Cuneate.
*Margin.*—Densely and minutely serrate.
*Texture of top surface.*—Soft, pubescent.
*Texture of bottom surface.*—Soft and pubescent with distinct veins.
*Color.*—Young foliage upper side: Near RHS Green N138B. Young foliage under side: Near RHS Greyed-Green 189C. Mature foliage upper side: Near RHS Green 138A. Mature foliage under side: Near RHS Greyed-Green 190B.
*Venation.*—Type: Pinnate. Venation color upper side: Near RHS Yellow-Green 147D. Venation color under side: Near RHS Greyed-Green 192B.
*Petiole.*—Length: About 2 mm to 3 mm. Diameter. About 3 mm. Color: Upper side: Near RHS Yellow-Green 147D. Lower side: Near RHS Greyed-Green 192B. Texture: Upper side: Soft and pubescent. Lower side: Soft and pubescent.

FLOWER

Flower arrangement: Cone-shaped panicle.
Flower type: Salverform.
Flowering habit: Freely flowering, panicles produced terminally and laterally.
Natural flowering season: Mid-summer to early fall.
Inflorescence height: Average 9 cm.
Inflorescence width: Average 3.5 cm.
Flower longevity on plant: 3-4 weeks.
Persistent or self-cleaning: Persistent.
Quantity of flowers per inflorescence: about 100 to 300.
Bud:
*Shape.*—Linear with protruding square cap.
*Length.*—7 mm.
*Diameter.*—2.5 mm.
*Color.*—Near RHS White N155C.
Flower size:
*Diameter.*—5 mm.
*Length.*—9 to 11 mm.
Petals:
*Appearance.*—Smooth, vibrant.
*Arrangement.*—Whorled.
*Petal length.*—3.0 mm.
*Petal width.*—2.0 mm.
*Quantity.*—4.
*Texture.*—Smooth.
*Apex.*—Obtuse.
*Shape.*—Obovate.
*Base.*—Fused.
*Margin.*—Slightly undulate.
Petal color:
*When opening.*—Upper surface: RHS White N155C. Lower surface: RHS White N155C.
*Fully opened.*—Upper surface: RHS White 155D. Lower surface: Near RHS White 155D.
*Fading to color.*—Upper. Near RHS Greyed-Orange 175A. Lower: Near RHS Greyed-Orange 175A.
Tube:
*Shape.*—Lanceolate to Ovate.
*Length.*—6.0 mm.
*Width.*—1.5 mm.
*Texture.*—Glabrous all surfaces.
*Color.*—Exterior Surface: Near RHS Red 50D. Interior Surface: Near RHS Red 49D.
Sepals:
*Quantity per flower.*—4
*Arrangement.*—Fused into calyx tube.
*Shape.*—Lanceolate to Ovate.
*Length.*—3.0 mm.
*Width.*—1 mm.
*Apex.*—Acute.
*Base.*—Cuneate.
*Margin.*—Entire.
*Texture.*—Upper: Slightly pubescent. Lower: Slightly pubescent.

*Color*.—Upper Surface: Near RHS Yellow-Green 145C. Lower Surface: Near RHS Yellow-Green 145C.

Peduncle:

*Length*.—1.3 to 2.5 cm.

*Diameter*.—3 mm.

*Angle*.—About 15 degrees, straight.

*Strength*.—Very strong.

*Texture*.—Softly pubescent.

*Color*.—Near RHS Yellow-Green 147D.

Pedicel:

*Length*.—1 mm.

*Diameter*.—Less than 1 mm.

*Angle*.—Outwardly facing.

*Strength*.—Good.

*Texture*.—Smooth.

*Color*.—Near RHS Yellow-Green 147D.

Fragrance: Moderate honey scent.

REPRODUCTIVE ORGANS

Stamens:

*Number*.—4

*Filament length*.—1.0 mm.

*Filament color*.—Near RHS Red 49D.

Anthers:

*Shape*.—Oblong.

*Length*.—1.0 mm.

*Color*.—Near RHS Red 49B.

*Pollen*.—Not observed.

Pistil:

*Number*.—1.

*Length*.—4.0 mm.

*Style*.—Length: 1.0 mm. Color: RHS Red 49D.

*Stigma*.—Shape: Oblong. Color: Near RHS Yellow-Green 145A. Ovary Color: RHS Yellow-Green 145A.

OTHER CHARACTERISTICS

Disease and pest resistance: Neither resistance nor susceptibility to additional normal diseases and pests of *Buddleia* has been observed.

Fruit/seed production: Seed production not observed, sterility not confirmed.

What is claimed is:

1. A new and distinct variety of *Buddleia* plant named 'TMBU08-3' as described and shown herein.

* * * * *